(12) United States Patent
Demers et al.

(10) Patent No.: US 6,696,249 B1
(45) Date of Patent: *Feb. 24, 2004

(54) METHOD FOR SCREENING FOR INHIBITORS AND ACTIVATORS OF TYPE III SECRETION MACHINERY IN GRAM-NEGATIVE BACTERIA

(75) Inventors: Brigitte Demers, Paris (FR); Philippe Sansonetti, Paris (FR); Claude Parsot, Paris (FR)

(73) Assignees: Institut Pasteur, Paris (FR); Institute National de la Santa et de la Recherche Medicale, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 09/674,307

(22) PCT Filed: May 12, 1999

(86) PCT No.: PCT/EP99/03582

§ 371 (c)(1),
(2), (4) Date: Feb. 5, 2001

(87) PCT Pub. No.: WO99/58714

PCT Pub. Date: Nov. 18, 1999

Related U.S. Application Data

(60) Provisional application No. 60/085,234, filed on May 13, 1998.

(51) Int. Cl.⁷ ............................. C12Q 1/68; C12N 1/20
(52) U.S. Cl. ......................................... 435/6; 435/252.3
(58) Field of Search .................................. 435/6, 252.3

(56) References Cited

FOREIGN PATENT DOCUMENTS

| WO | WO 97/40063 | 10/1997 |
|----|-------------|---------|
| WO | WO 99/45136 | 9/1999 |

OTHER PUBLICATIONS

Sasakawa et al (J Bacteriol 1993 vol 175(8) p. 2334–46).*
Hartman et al. (J. Bacteriology 1990 vol. 172(4) pp. 1905–1915).*
Uchiya et al. (Molecular Microbiol. 1995 vol. 17(2) pp. 241–250).*

Demers, B., et al., "Induction of type III secretion in *Shigella f lexneri* is associated with dif ferential control of transcription of genes encoding secreted proteins", T he EMBO Journal, vol. 17, No. 10, (1998), pp. 2894–2903.

Demers, B., et al., "Expression of secreted proteins is controlled by the activity of the type III secretion machinery of *Shigella flexneri*", Abstracts of the Interscience Conference on Antimirobial Agents and Chemotherapy, vol. 37, (1997), pp. 34.

Abdelmounaaïm Allaoui, et al., "Characterization of the *Shigella flexneri* ipgD and ipgF genes, which are located in the prox imal part of the mxi locus", Infection and Immunity, US, America Society for Microbiology, vol. 61, pp. 1707–1714 (1993).

Ménard, R., et al., "The secretion of the *Shigella flexneri* Ipa invasins is activated by epithelial cells and controlled by IpaB and IpaD", The EMBO Journal, vol 13, no 22, (1994), pp. 5293–5302.

Allaoui, A., et al., "MxiD, an outer membrane protein necessary for the secretion of the *Shigella flexneri* Ipa invasins", Molecular Microbiology, vol. 7, No. 1, (1993). pp. 59–68.

Pettersson, J., et al., "Modulation of virulence factor expression by pathogen target cell contact", Science, vol. 273, (1996), pp. 1231–1233.

Demers, B., et al., "The multifunctional Mxi–Spa system of Shigella", Abstracts of the General Meeting of the American Society for Microbiology, vol 98, (1998), p. 25.

* cited by examiner

*Primary Examiner*—Mark Navarro
(74) *Attorney, Agent, or Firm*—Finnegan Henderson Farabow Garrett & Dunner

(57) ABSTRACT

This invention relates to mutant strains of gram-negative bacteria that constitutively secrete proteins via the type III secretion machinery and to methods of identifying molecules that are able to activate or inhibit secretion in wild-type strains of gram-negative bacteria by exposing gram-negative bacterial cells to a sample molecule, wherein the bacterial cells contain a reporter gene transcriptionally fused to a promoter of a gene activated or regulated by the type III secretion machinery and detecting the presence or activity of the product of the reporter gene.

3 Claims, 4 Drawing Sheets

SEQUENCE LISTING

```
<160> NUMBER OF SEQ ID NOS: 5

<210> SEQ ID NO 1
<211> LENGTH: 10
<212> TYPE: PRT
<213> ORGANISM: Shigella flexneri

<400> SEQUENCE: 1

Met Gln Thr Ser Asn Ile Thr Asn His Glu
  1               5                  10

<210> SEQ ID NO 2
<211> LENGTH: 14
<212> TYPE: PRT
<213> ORGANISM: Shigella flexneri

<400> SEQUENCE: 2

Ile Ile Thr Phe Gly Ile Tyr Ser Pro His Glu Thr Leu Ala
  1               5                  10

<210> SEQ ID NO 3
<211> LENGTH: 11
<212> TYPE: PRT
<213> ORGANISM: Shigella flexneri

<400> SEQUENCE: 3

Val His Thr Ile Thr Ala Pro Val Ser Gly Asn
  1               5                  10

<210> SEQ ID NO 4
<211> LENGTH: 12
<212> TYPE: PRT
<213> ORGANISM: Shigella flexneri

<400> SEQUENCE: 4

Met Leu Pro Ile Asn Asn Asn Phe Ser Leu Pro Gln
  1               5                  10

<210> SEQ ID NO 5
<211> LENGTH: 15
<212> TYPE: PRT
<213> ORGANISM: Shigella flexneri

<400> SEQUENCE: 5

Tyr Glu Met Leu Glu Asn Glu Tyr Pro Gln Arg Val Ala Asp Arg
  1               5                  10                  15
```

METHOD FOR SCREENING FOR INHIBITORS AND ACTIVATORS OF TYPE III SECRETION MACHINERY IN GRAM-NEGATIVE BACTERIA

This application claims the benefit of provisional application No. 60/085,234, filed May 13, 1998, the content of which is incorporated herein by reference.

This invention relates to the field of biochemical assays involving regulated expression of reporter genes, and to mutant strains of bacteria useful in biochemical assays. More particularly, it relates to methods of screening for molecules capable of affecting expression and/or activity of type III secretion machinery in gram-negatve bacteria.

Type III secretion machinery is present in numerous gram-negative bacteria (including members of the species Shigella, Salmonella, Yersinia, Eschedchia, Pseudomonas, Xanthomonas, Ralstonia, and Erwinia) that are pathogenic for man, animals, and plants. For example, the Sec-independent type III secretion pathway is involved in secretion of Yersinia anti-host proteins. In Salmonella and Shigella species, it is involved in the process of entry into epithelial cells. It is also implicated in EPEC signal transducing proteins, *Pseudomonas aeruginosa* toxins, and virulence factors of many plant pathogens, as well as in flagellum assembly of bacteria such as *S. typhimurium* and *Bacillus subtilis*.

Features of this secretion pathway can include activation of secretion by contact of the bacterium with host cells (Ménard et al., 1994, "The secretion of the *Shigella flexneri* Ipa invasins is activated by epithelial cells and controlled by IpaB and IpaD.", *EMBO J.*, 13:5293–5302; Watarai et al., 1995, "Contact of Shigella with host cells triggers release of Ipa invasins and is an essential function of invasiveness.", *EMBO J.*, 14:2461–2470; Zierler and Galan, 1995, "Contact with cultures epithelial cells stimulates secretion of *Salmonella typhimurium* invasion proteins InvJ.", *Infect. Immun.*, 63:4024–4028); that some of the secreted proteins are delivered into the cytoplasm of host cells (Rosqvist et al., 1994, "Target cell contact triggers expression and polarized transfer of Yersinia YopE cytotoxin into mammalian cells.", *EMBO J.*, 13:964–972; Sory and Cornelis, 1994, "Translocation of an hybrid YopE-adenylate-cyclase from *Yersinia enterocolitica* into HeLa cells.", *Mol. Microbiol.*, 14:583–594; Wood et al., 1996, "SopE, a secreted protein of *Salmonella dublin*, is translocated into the target eukaryotic cell via a sip-dependent mechanism and promotes bacterial entry.", *Mol. Microbiol.*, 22:327–338; Collazo and Galan, 1997, "The invasion-associated type III system of *Salmonella typhimurium* directe the translocation of Sip proteins into the host cell.", *Mol. Microbiol*, 24:747–756); and that transcription of genes encoding secreted proteins is controlled by secretion of regulatory proteins (Hughes et al., 1993, "Sensing structural intermediates in bacterial flagellar assembly by export of a negative regulator.", *Science*, 262:1277–1280; Pettersson et al., 1996, "Modulation of virulence factor expression by pathogen target cell contact.", *Science*, 273:1231–1233).

Based on the observations that (1) the secretion machinery is involved in secretion of factors which are active against the host, and (2) secretion mutants are avirulent, the type III secretion machinery provides an attractive target for the screening of molecules that would prevent or inhibit gram-negative bacteria from secreting their virulence factors. However, the search for molecules capable of inhibiting the secretion mechanism has previously required two conditions to be present. First, the type III secretion machinery must be active. And second, the product of the secretion activity, i.e., the secreted proteins, must be measurable. Unfortunately, the secretion machinery is, at best, only weakly active when bacteria are grown in standard laboratory media, making the search for inhibitor molecules difficult or impossible. In addition, there is no way to easily measure the presence of a protein secreted in the culture medium by the type III secretion machinery. These proteins do not have an easily assayable enzymatic activity and their secretion must be evaluated using ELISA, which is time consuming and expensive.

This invention provides mutant strains of gram-negative bacteria that constitutively secrete proteins via the type III secretion machinery.

This invention also provides methods of identifying molecules that are able to activate or inhibit secretion in wild-type strains of gram-negative bacteria. These methods comprise the steps of:

a) exposing gram-negative bacterial cells to a sample molecule, wherein said bacterial cells contain a reporter gene transcriptionally fused to a promoter of a gene activated or regulated by the type III secretion machinery; and b) detecting the presence or activity of the product of the reporter gene.

To practice the methods of this invention, genes under transcriptional control of the type III secretion machinery are identified. Transcriptional fusions between the promoters of these genes and a reporter gene, such as the lacZ reporter gene, are constructed and introduced into wild-type gram-negative bacteria and mutants of these bacteria that constitutively secrete proteins via the type III secretion machinery or are deficient for secretion via the type III secretion machinery. The presence (or activity) of the reporter gene product is evaluated under conditions leading to active secretion to demonstrate that the transcriptional activity of these promoters can be used as an indicator of the secretion activity of the type III secretion machinery.

Using Shigella as a model system for the screening of inhibitors of type III secretion, five genes under transcriptional control of the type III secretion machinery have been identified and the promoters of these genes have been used to create transcriptional fusions with the reporter gene, lacZ. β-galactosidase activity can be induced in recombinant Shigella cells harboring these transcriptional fusion constructs under conditions known to lead to active secretion.

Any gram-negative bacteria containing type III secretion machinery may be used in the methods of this invention. Suitable bacteria include members of the species Shigella, Salmonella, Yersinia, Escherichia, Pseudomonas, Xanthomonas, Ralstonia, and Erwinia. Similarly, any suitable reporter gene may be used to create a transcriptional fusion construct for use in the methods of this invention. Some suitable reporter genes are, for example, lacZ, phoA, luxAB, and gfp. In a preferred method of this invention, the reporter gene is the lacZ gene.

In one method of the invention, the promoter is from a gene selected from the group consisting of virA and the ipaH family of genes, particularly, ipaH9.8, ipaH7.8, ipaH4.5, and ipaH1.4. Promoters such as ipgD, icsB, ipaA, and mxiD are not regulated by the secretion machinery and thus may be used in the methods of this invention as internal controls. Other suitable promoters for use in the methods of this invention may be easily identified following the teachings detailed in this specification.

In a preferred method according to this invention, candidate inhibitor molecules are screened against three strains of bacteria which contain a reporter gene transcriptionally fused to a promoter of a gene regulated by the activity of the type III secretion machinery: a strain in which secretion is regulated, a strain which has a phenotype of constitutive secretion, and a strain which is deficient for secretion.

Figure 1:
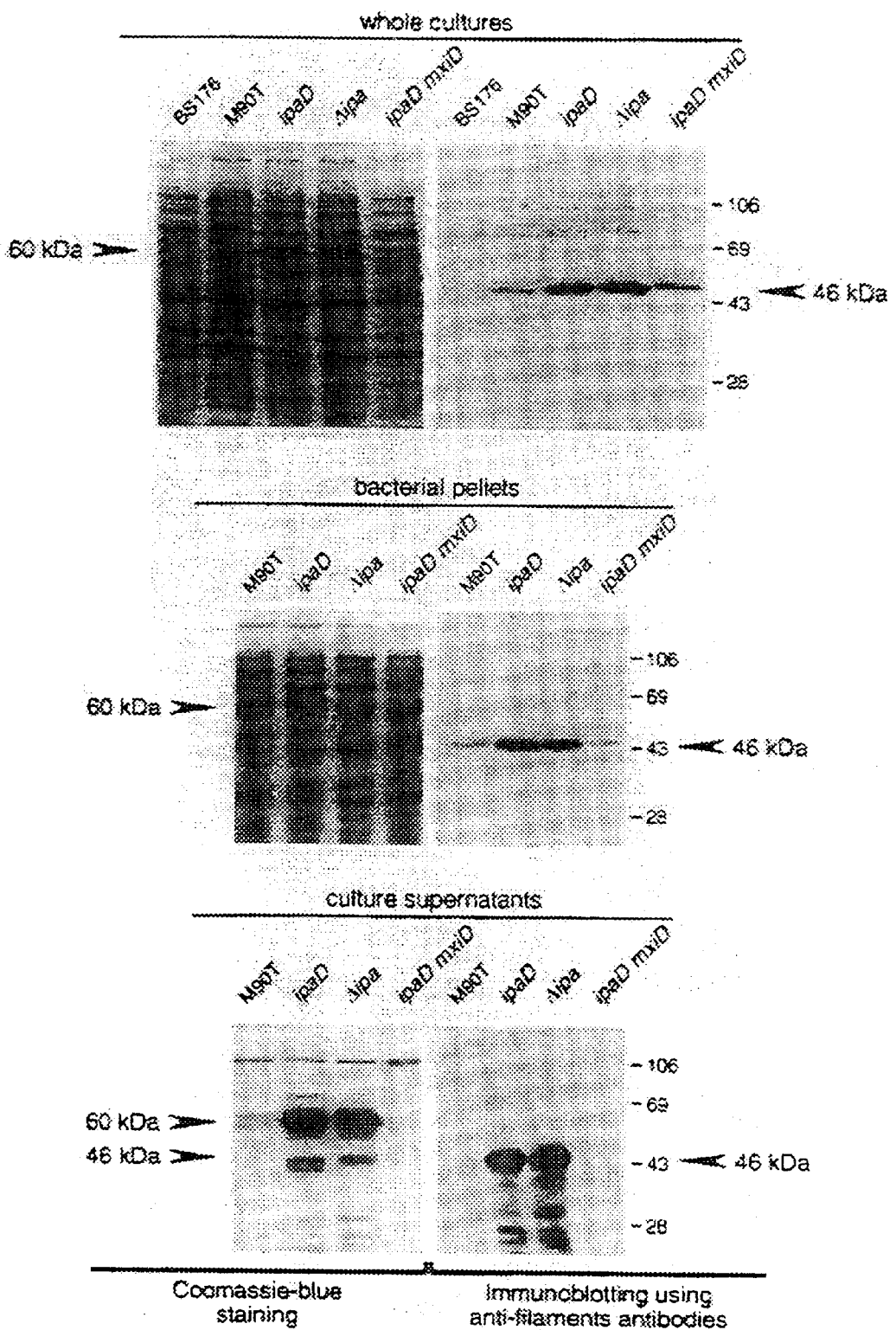
FIG. 1 depicts secretion of proteins by various Shigella strains. Cultures of M90T (wild type), BS176 (the virulence plasmid-cured strain), and the ipaD (SF622), ΔipaBCDA (SF635), and ipaD mxiD (SF634) mutants were used to prepare either whole culture extracts, by adding Laemmli sample buffer directly to the cultures, or bacterial pellets and culture supernatants, by centrifugation of the cultures. Proteins present in culture supernatants were concentrated 10 times by TCA precipitation. Samples were separated by SDS-PAGE and analyzed by either Coomassie blue staining or immunoblotting using an antiserum raised against aggregated recovered from the medium of the ΔipaBCDA mutant. Numbers indicate the position and the size (in kDa) of standard proteins and arrows indicate the position of the 60- and 46-kDa proteins.

Production of most bacterial virulence factors is tightly regulated in response to environmental signals. In Shigella, for example, both the temperature and the osmolarity of the growth medium modulate transcription of genes involved in entry of the bacteria into epithelial cells (Bernardini et al., 1990, "The two-component regulatory system OmpR-EnvZ controls the virulence of Shigella.", "*J. Bacteriol.*, 172:6274–6281; Maurelli et al., 1984, "Temperature-dependent expression of virulence genes in Shigella species.", *Infect. Immun.*, 43:195–201). In addition, contact of Shigella with epithelial cells (Ménard et al., 1994; Watarai et al., 1995) and exposure of the bacteria to Congo red (Sankaran et al., 1989, "Congo-red mediated regulation of levels of *Shigella flexneri* 2a membrane proteins.", *Infect. Immun.*, 57:2364–2371; Parsot et al., 1995, "Enhanced secretion through the *Shigella flexneri* Mxi-Spa translocon leads to assembly of extracellular proteins into macromolecular structures." *Mol. Microbiol*, 16, 291–300.; Bahrani et al., 1997) or bile salts (Pope et al., 1995) activate secretion of IpaB and IpaC.

The Shigella Model

Shigella was used as a model system for application of the methods of this invention. Members of the genus Shigella cause bacillary dysentery in humans by invading the colonic epithelial mucosa and inducing a strong inflammatory response (LaBrec et al., 1964). In vitro, cell invasion involves two steps: entry and intercellular dissemination. Genes involved in both steps are carried on a 200-kb virulence plasmid (reviewed by Hale, 1991; Parsot, 1994). A 31-kb fragment of this plasmid is necessary and apparently sufficient for entry into epithelial cells (Maurelli et al, 1985; Sasakawa et al., 1988). This fragment is organized in two divergently transcribed regions which, schematically, encode secreted proteins, the IpaA-D proteins, and a type III secretion system, the Mxi-Spa secretion apparatus. The first region contains eight genes, including ipaBCDA, which are transcribed from a promoter located upstream from icsB. The second region contains 20 genes, designated ipg, mxi, and spa, which are clustered in large operons. Inactivation of ipa, mxi, and spa genes leads to a non-invasive phenotype, due to either loss of effector proteins (Sasakawa et al., 1989; Ménard et al., 1993) or failure to secrete them (Andrews and Maurelli, 1992; Venkatesan et al., 1992; Allaoui et al., 1993b; Sasakawa et al., 1993).

Bacterial Strains and Growth Media

All *Shigella flexneri* strains identified in Table I are derivatives of the wild-type strain M90T (Sansonetti et al., 1982). Bacteria were grown in Luria-Bertani (LB) medium or tryptic soy (TCS) broth. Antibiotics were used at the following concentrations: ampicillin, 100 μg/ml; kanamycin, 30 μg/ml; and streptomycin, 100 μg/ml. Congo red (SERVA, Heidelberg, Germany) was used to induce secretion by bacteria growing in LB medium.

Constitutively Secreting Strains

Only a small proportion of IpaA-D proteins is secreted by wild-type Shigella growing in laboratory media. Inactivation of ipaD enhances secretion of IpaA, IpaB, IpaC, and about 15 other proteins (Ménard et al., 1994; Parsot et al., 1995). These latter proteins are absent or barely detectable in the medium of the wild-type strain unless Congo red, a dye that induces secretion (Bahrani et al., 1997), is present in the culture medium (Parsot et al., 1995).

Inactivation of either ipaB or ipaD and deletion of the ipaB, C, D, and A genes lead to the secretion of about 15 proteins that associate in the extracellular medium (Parsot et al., 1995). Aggregates containing proteins secreted by the ΔipaBCDA mutant (SF635) were used to immunize mice and the resulting anti-serum was tested by Western blotting on extracts of whole cultures, bacterial pellets, and culture supernatants of M90T (wild-type), SF622 (ipaD), SF635 (ΔipaBCDA), SF634 (ipaD mxiD), and BS176 (a virulence-plasmid cured-stain). The serum reacted most strongly with a 46-kDa protein. This protein was present in high amounts in extracts of ipaD and ΔipaBCDA strains; was present in low amounts in extracts of wild-type and ipaD mxiD strains; and was not present in extracts of the virulence plasmid-cured strain (FIG. 1). SDS-PAGE analysis and Coomassie blue staining also revealed that a protein, or possibly a mixture of proteins of about 60 kDa was present in higher amounts in extracts of the ipaD and ΔipaBCDA strains than in extracts of the wild-type and ipaD mxiD strains (FIG. 1). These results suggested that production of 46-kDa and 60-kDa secreted proteins was increased in the constitutively secreting ipaD and ΔipaBCDA strains as compared to the wild-type and secretion deficient ipaD mxiD strains.

Characterization of the Gene Encoding the 46-kDa Secreted Protein

Figure 2:
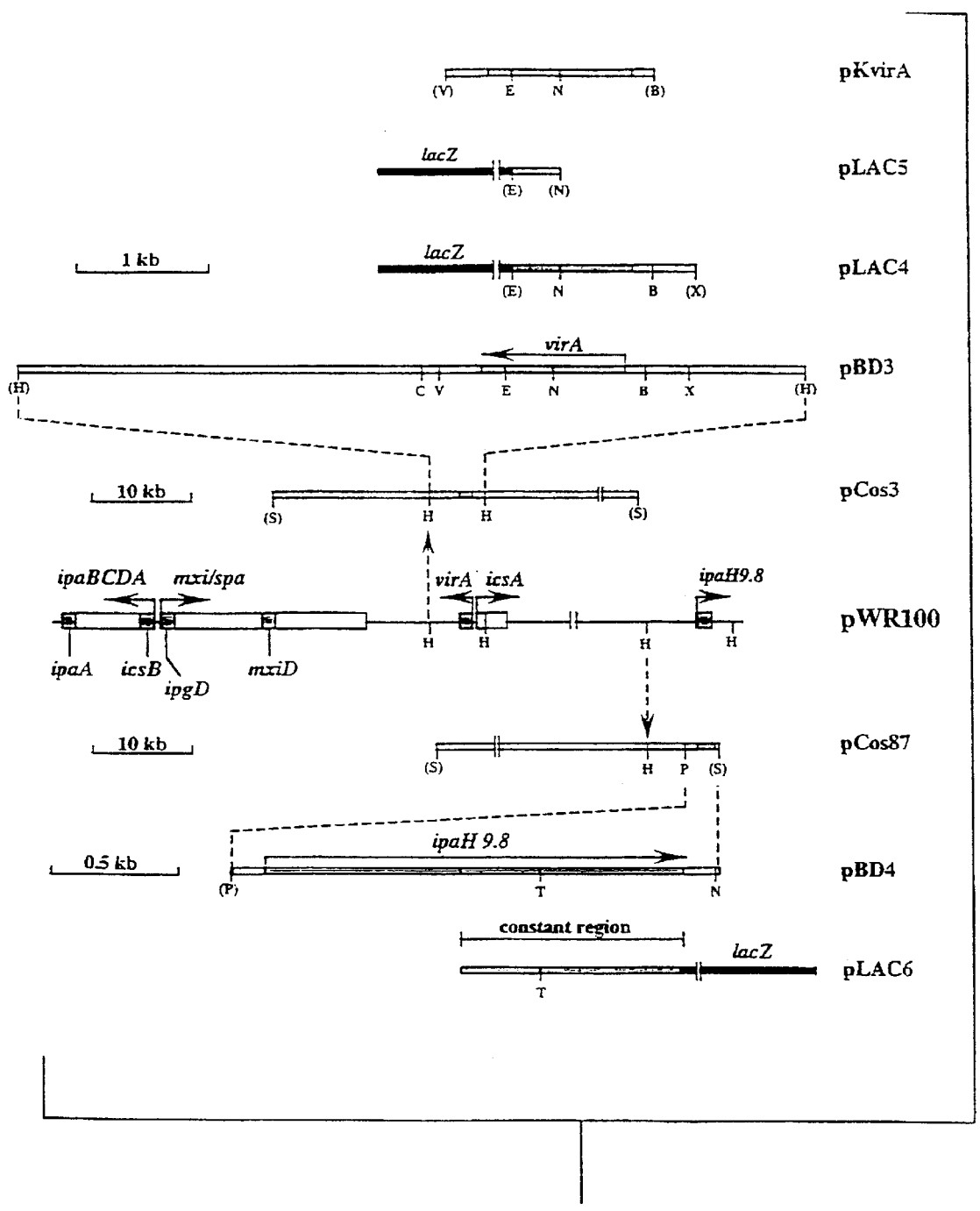
FIG. 2 depicts the structure of plasmids carrying virA and ipaH9.8. A schematic genetic map of a portion of the virulence plasmid pWR100 is shown in the center, along with the position of some relevant restriction sites. Symbols used for restriction sites are: B, BspEI; C, HincII; E, EcoRI; H, HindIII; N, NdeI; P, HpaI; S, Sau3AI; T, StuI; V, BbvI; X, XbaI. The DNA corresponding to virA and ipaH9.8 is shown by shaded bars and the lacZ gene by a solid bar. Arrows indicate the orientation of transcription of the genes. Restriction sites of the virulence plasmid that were used for cloning are indicated in brackets.

The 46-kDa protein secreted by the ΔipaBCDA mutant was transferred onto a PVDF membrane and subjected to Edman degradation and proteolysis by endolysin. The N-terminal sequence of the protein was identified as M-Q-T-S-N-I-T-N-H-E (SEQ ID NO: 1) and those of two internal peptides as I-I-T-F-G-I-Y-S-P-H-E-T-L-A (SEQ ID NO: 2) and V-H-T-I-T-A-P-V-S-G-N (SEQ ID NO: 3). Oligonucleotides based on the N-terminal sequence and one internal peptide were used to screen, by Southern blotting, a set of overlapping cosmids representing the entire virulence plasmid. Both probes hybridized to a 6.4 kb HindIII fragment of cosmid pCos3, which was then cloned into pUC19 to give rise to pBD3 (FIG. 2).

Subcloning experiments and Southern blot analysis of recombinant plasmids using oligonucleotides as probes allowed us to localize the gene encoding the 46-kDa protein on a 3.2-kb HindII-HindIII fragment located upstream from icsA (Bernardini et al., 1989; Lett et al, 1989). Sequence analysis revealed an open reading frame (ORF) starting 487 bp upstream from the icsA translation start codon and oriented in the opposite direction. Amino acid sequences deduced from positions 43 to 71, 159 to 200, and 442 to 473 of the ORF were identical to those determined for the N-terminal end and the two internal peptides of the secreted protein. These sequence data have been submitted to the DDBJ/EMBL/GenBank databases under the accession number AF047364. The deduced sequence of the 46-kDa protein was identical to that of VirA, a secreted protein encoded by the virulence plasmid of a S. flexneri strain of serotype 2a (Uchiya et. al, 1995) and, therefore, the corresponding gene of S. flexneri 5 was designated virA. No other ORF was detected immediately upstream or downstream from virA. Restriction analysis of overlapping cosmids indicated that virA was located about 10 kb downstream from the spa operon (Venkatesan et al., 1992; Sasakawa et al., 1993) on the virulence plasmid pWR100.

Characterization of the Gene Encoding a 60-kDa Secreted Protein

The 60-kDa proteins, which were secreted in high amount by the ΔipaBCDA strain, were transferred into a PVDF membrane and the lower part of the band was used for N-terminal sequence determination and proteolysis by endolysin. Analysis of the N-terminal sequence indicated that the sample contained two proteins; the sequence of the major species was determined as M-L-P-I-N-N-N-F-S-L-P-Q (SEQ ID NO: 4). The sequence of an internal peptide was determined as Y-E-M-L-E-N-E-Y-P-Q-R-V-A-D-R (SEQ ID NO: 5), which was almost identical to a fragment of the constant region of members of the IpaH family. IpaH proteins are characterized by a constant C-terminal region of about 300 residues, which is preceded by a variable N-terminal region composed of repetitive motifs (Hartman et al., 1990; Venkatesan et al., 1991). The N-terminal sequence of the 60-kDa secreted protein was different from those deduced from the 5' end of ipaH7.8, ipaH4.5, ipaH2.5 and ipaH1.4 (Hartman et al., 1990; Venkatesan et al., 1991), which suggested that this protein might correspond to the fifth IpaH protein, IpaH9.8, whose gene had not been sequenced yet.

Southern blot analysis using a probe derived from the constant region of ipaH genes indicated that ipaH9.8 was present in cosmid pCos87. Deletion derivatives of pCos87 were constructed to give rise to pBD4 (FIG. 2), whose 2.4-kb insert was entirely sequenced. The amino acid sequences deduced from positions 40 to 75 and 1477 to 1521 of the ORF identified by sequence analysis were identical to those of the N-terminal end and of the internal peptide of the 60-kDa secreted protein. These sequence data have been submitted to the DDBJ/EMBL/GenBank databases under the accession number AF047365. The ipaH9.8 gene encodes a 545-residue protein with a deduced Mr of 61,886. No ORFs were identified upstream or downstream from ipaH9.8. Restriction analysis of overlapping cosmids indicated than ipaH9.8 was located 45 kb downstream from the spa operon.

DNA analysis, PCR, plasmid construction, and transformation of E. coli and S. flexneri strains were performed according to standard methods. Nucleotide sequences were determined by the dideoxy chain termination procedure on alkaline-denaturated plasmid DNA. Overlapping cosmids representing the entire virulence plasmid were previously constructed by inserting 40-kb fragments of pWR100 into the vector pJB8 (Maurelli et al, 1985).

Inactivation of ipaD Increases Transcription of virA and ipaH Genes

Western blot analysis indicated that a higher amount of VirA was produced by the ipaD mutant than by the wild-type strain (FIG. 1). To investigate virA transcription, we constructed a virA-lacZ transcriptional fusion. Plasmid pLAC4 (FIG. 2) was constructed by cloning a 1.5-kb XbaI-EcoRI fragment that contains the 5' part of icsA, the icsA-virA intergenic region, and the 5' part of virA, into the SmaI site located upstream from the lacZ reporter gene in the suicide plasmid pLAC1 that confers resistance to ampicillin (Allaoui et al., 1992). (Plasmid pLAC4 was deposited in the Collection Nationale de Cultures de Microorganismes in Paris, France on May 13, 1998 under accession No. 1–2015.) pLAC4 was then transferred by conjugation into M90T-Sm and SF622 (ipaD2) to produce recombinant strains SF1001 and SF1002. Since pLAC4 does not replicate in S. flexneri, the Ap' clones arose through homologous recombination between the identical sequences carried by the virulence plasmids M90T-Sm or SF622 and the recombinant p1 asmid pLAC4, thereby placing the lacZ reporter gene under the control of the virA promoter. Expression of the virA-lacZ fusion was 17 times higher in the ipaD$^-$ strain as compared to the ipaD$^+$ strain (Table II), indicating that the increased production of VirA by the ipaD mutant was due to an increased transcription of virA. Southern analysis confirmed the structure of the pWR100 derivatives carrying the virA-lacZ transcriptional fusion in recombinant strains designated SF1001 (virA-lacZ virA$^-$ipaD$^+$) and SF1002 (virA-lacZ virA$^+$ipaD$^-$).

Plasmid pLAC5 (FIG. 2) was constructed by deleting a NdeI-EcoRI fragment from pLAC4 and thus contains a 380-bp fragment internal to the virA gene. To determine whether VirA is involved in the regulation of the virA promoter, pLAC5 was integrated at the virA locus of the wild-type and ipaD to produce recombinant strains SF1003 and SF1004. Integration of pLAC5 into the virA locus of pWR100 also placed the lacZ gene under the control of the virA promoter but, unlike that of pLAC4, led to the disruption of the virA gene. Inactivation of virA had no effect or transcription of the virA-lacZ fusion in either the ipaD$^+$ or ipaD$^-$ backgrounds, indicating that virA was not autoregulated. Southern analysis confirmed the structure of the pWR100 derivatives carrying the virA-lacZ transcriptional fusion in recombinant strains designated SF1003 (virA-lacZ virA$^-$IpaD$^+$) and SF1004 (virA-lacZ virA$^-$ipaD$^+$).

To analyze transcription of the various ipaH genes, the constant region of ipaH9.8 was amplified using the polymerized chain reaction (PCR) technique, and the PCR product was cloned between the KpnI and XbaI sites that are located upstream from the lacZ gene in the suicide vector pLAC2 (Allaoui et al., 1993a) to construct plasmid pLAC6. pLAC6 was then transferred by conjugation into M90T-Sm (wild-type) and SF622 (ipaD). Since pLAC6 carried the constant region of ipaH, integration of the suicide plasmid could occur into any of the five ipaH genes carried on the virulence plasmid. In each case, the lacZ reporter gene is placed under the control of the promoter of the ipaH gene into which the plasmid is integrated. Transconjugants were screened by Southern blot analysis of their virulence plasmid digested by HindIII using a probe from the ipaH constant region. The strains were designated SF1005 (ipaH9.8-lacZ ipaD$^+$), SF1006 (ipaH9.8-lacZ ipaD$^-$), SF1007 (ipaH7.8-lacZ ipaD$^-$), SF1008 (ipaH4.5-lacZ ipaD$^+$), SF1009 (ipaH4.5-lacZ ipaD$^-$), SF 1010 (ipaH1.4-lacZ ipaD$^+$), SF1011 (ipaH1.4-lacZ ipaD$^-$). The ipaH2.5-lacZ fusion in the wild-type background as well as the ipaH7.8-lacZ and ipaH2.5-lacZ fusions in the ipaD background were not obtained. Expression of ipaH9.8-, ipaH4.5-, and ipaH1.4-lacZ fusions was low in derivatives of the wild-type strain and was increased 5–20 times in derivatives of the ipaD mutant (Table II).

To investigate transcription of genes of the entry region, we used lacZ transcriptional fusions in icsB and ipaA, which are the first and last genes of the ipaBCDA operon, respectively, and in ipgD and mxiD, which are the first and 12th genes of the mxi operon, respectively (FIG. 2). These fusions were constructed in both the wild-type and ipaD strains. For example, construction of the ipgD-lacZ fusion was achieved using the suicide plasmid pLAC3 (Allaoui et al. 1993a). The recombinant plasmid pLAC3 (Allaoui et al., 1993) was constructed by cloning a 1.4-kb SspI fragment that contains the 5' part of icsB, the icsB-ipgD intergenic region, and the 5' part of ipgD (Allaoui et al., 1992, 1993) into the SmaI site located upstream from the lacZ reporter gene in the vector pLAC1 (Allaoui et al., 1992). (Plasmid pLAC3 was deposited in the Collection Nationale de Cultures de Microorganismes in Paris, France on May 13, 1998 under accession No. I-2014.) pLAC3 was then transferred by conjugation into M90T-Sm and SF622 (ipaD2) to produce recombinant strains SF134 and SF806. Since pLAC3 does not replicate in *S. flexneri*, the Ap$^r$ clones arose through homologous recombination between the identical sequences carried by the virulence plasmids M90T-Sm or SF622 and the recombinant plasmid pLAC3, thereby placing the lacZ reporter gene under the control of the virA promoter. Southern analysis confirmed the structure of the virulence plasmid carrying the ipgD-lacZ transcriptional fusion in the recombinant strains designated SF134 (ipgD-lacZ ipaD$^+$) and SF806 (ipgD-lacZ ipaD$^-$). Integration of the suicide plasmids used to construct these fusions did not affect the secretion phenotype of recombinant strains. For each fusion, similar amounts of -galactosidase were present in derivatives of the wild-type and ipaD strains, indicating that transcription of these genes was not affected by inactivation of ipaD (Table II).

Congo Red Increases Transcription of virA and ipaH Genes

Secretion of IpaB and IpaC is enhanced when bacteria grow in the presence of Congo red (Parsot et al, 1995). To investigate the effect of Congo red on virA transcription, we assayed the β-galactosidase activity in strain SF1001 (virA-lacZ ipaD$^+$) after growth in the presence of various concentrations of Congo red. Transcription of the virA-lacZ fusion was low at concentrations of dye up to 20 μg/ml and then increased with the concentration of the dye to reach a plateau at about 100 μg/ml of Congo red. Likewise, about 3–12 times more β-galactosidase activity was present in strains carrying ipaH9.8-, ipaH7.8-, ipaH4.5-, and ipaH1.4-lacZ fusions after growth in the presence of 100 μg/ml of Congo red (Table II). In contrast, transcription of icsB-, ipaA-, ipgD-, and mxiD-lacZ fusions was not affected by the presence of Congo red in the growth medium (Table II).

Secretion is Required for Activation of virA Transcription

To determine whether regulation of virA transcription was dependent on the type III secretion machinery, we compared the β-galactosidase activities produced by the virA-lacZ fusion in derivatives of wild-type (SF1001) and mxiD (SF1012) strains during growth in the presence of Congo red and we compared the production of VirA in ipaD and mxiD ipaD strains.

The presence of Congo red in the growth medium of the derivative of the mxiD strain carrying the virA-lacZ fusion did not lead to an increase in β-galactosidase activity (Table II), and lesser amounts of VirA were present in the ipaD mxiD strain as compared to the ipaD strain (FIG. 1). This indicated that activation of the virA promoter in response to Congo red and inactivation of ipaD required the integrity of the secretion machinery.

Figure 3:
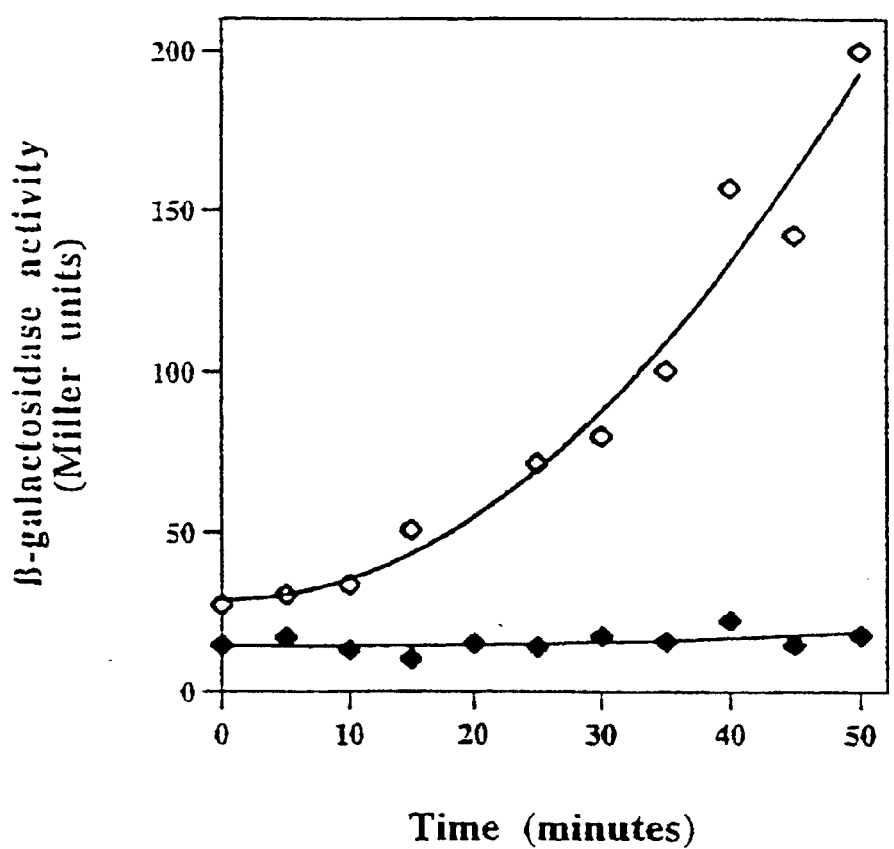
FIG. 3 depicts transcription of the virA-lacZ fusion upon addition of Congo red to the growth medium. Congo red (100 μg/ml) was added to the growth medium during the exponential phase of growth of derivatives of the wild-type (open symbols) and mxiD (closed symbols) strains carrying the virA-lacZ fusion. Samples were then collected at 5 min intervals and assayed for β-galactosidase activity. For both strains, no increase in β-galactosidase activity was detected in the absence of Congo red.
Figure 4:
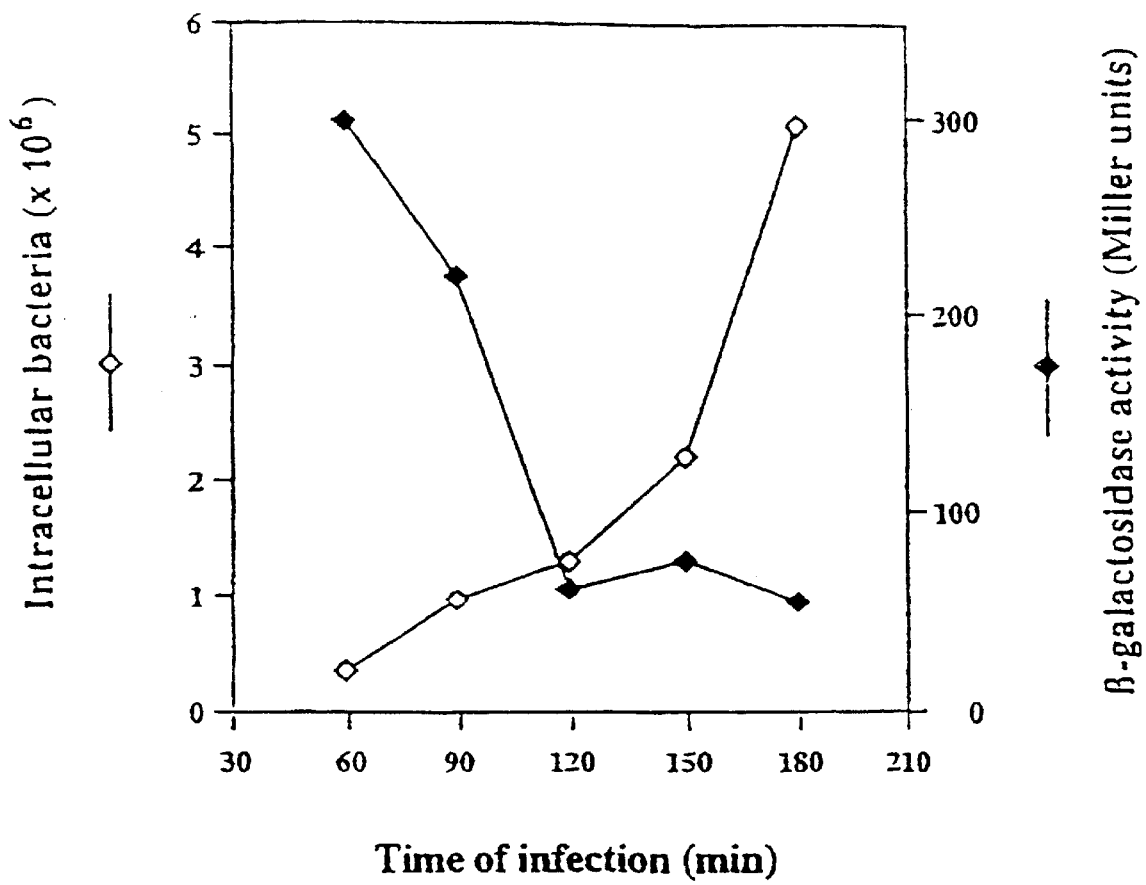
FIG. 4 depicts transcription of the virA-lacZ fusion by intracellular bacteria; Intracellular bacteria recovered after various times of infection of HeLa cells by SF1001 (virA-lacZ) were numbered by plating (open symbols) and used to assay β-galactosidase activity (closed symbols).

To investigate kinetics of activation of the virA promoter, Congo red (100 μg/ml) was added to the growth medium during the exponential phase of growth of derivatives of the wild-type and mxiD strains carrying the virA-lacZ fusion. Samples were then collected at 5 min intervals and assayed for β-galactosidase activity. An increase in the β-galactosidase specific activity was detected 10 min after addition of the dye to the medium of the derivative of the wild-type strain, whereas no transcriptional activation of the virA-lacZ fusion was detected in the derivative of the mxiD mutant (FIG. 3).

These results differentiated the virA and ipaH genes, the transcription of which was increased after growth in the presence of Congo red or by inactivation of ipaD, from the genes of the entry region, the transcription of which was apparently constitutive with respect to these parameters. Moreover, this suggested that transcription of the virA and ipaH genes was regulated by the Mxi-Spa secretion machinery, since (i) conditions leading to an enhanced transcription of these genes were the same as those known to increase secretion through the Mxi-Spa secretion machinery, and (ii) in these conditions, the secretion machinery was required for the enhanced transcription of the virA-lacZ fusion and for the enhanced production of the VirA protein.

Transcription of virA- and ipaH-lacZ Fusions Upon Entry and During Intracellular Multiplication To investigate virA and ipaH transcription during infection of epithelial cells, we measured the β-galactosidase activity that was present in bacteria shortly after entry into epithelial cells. HeLa cells were infected as previously described (Sansonetti et al., 1986). Briefly, cells were infected for 30 minutes to allow entry and then treated with gentamicin for 30 minutes to kill extracellular bacteria. Infected cells were then washed to remove killed bacteria and lyzed, and intracellular bacteria were recovered by centrifugation. The number of intracellular bacteria was determined by plating and the β-galactosidase activity present in these bacteria was assayed by using MUG as a substrate. The specific activity was first expressed in units of fluorescence per bacterium and then converted into Miller units. For the strain carrying the ipgD-lacZ fusion, chosen as a representative of genes which were expressed constitutively in vitro, the β-galactosidase activity present within intracellular bacteria recovered after 60 min of infection was similar to that found after growth in laboratory medium (Table III). This confirmed that, following gentamicin treatment, washes of infected cells were sufficient to remove killed extracellular bacteria which, otherwise, could have contributed to the total β-galactosidase activity without being numbered by plating. For strains carrying the virA- and ipaH-lacZ fusions, the β-galactosidase activity was 6 to 30 times higher in intracellular bacteria than in bacteria grown in vitro (Table III). This indicated that transcription of virA, ipaH9.8, ipaH7.8, ipaH4.5 and ipaH1.4 had been induced upon entry or shortly thereafter.

To investigate virA transcription during growth in the intracellular compartment, infected cells were lyzed after various periods of incubation in the presence of gentamicin and intracellular bacteria were counted by plating and assayed for β-galactosidase activity. The number of intracellular bacteria carrying the virA-lacZ fusion increased with the time of incubation, which was consistent with their intracellular multiplication (FIG. 3). In contrast, the specific β-galactosidase activity present in these bacteria decreased steadily, suggesting that the decrease in specific activity was due to bacterial multiplication. Similarly, the β-galactosidase activity present in bacteria carrying the various ipaH-lacZ fusions was 6 to 13 times lower after 150 min of infection as compared to the activity present after 60 min of infection (Table III). These results suggested that the virA- and ipaH-lacZ fusions had not been transcribed between 60 and 150 min of infection. In contrast, for the strain carrying the ipgD-lacZ fusion, similar amounts of β-galactosidase were present after 60 and 150 min of infection (Table II), suggesting that the intracellular compartment had no effect on ipgD transcription.

Protein Analysis

All protein analyses were carried out according to the following protocol. Aggregated proteins were collected from the culture medium of SF635 (Δipa) and solubilized in 0.1% SDS. Mice were injected twice with this preparation, at one week interval. Sera were collected the fourth week, pooled, and absorbed on sonicated extracts of BS176.

Bacteria in the exponential phase of growth were harvested by centrifugation at 14,000 g for 10 min. Crude extracts were obtained from the bacterial pellet, and proteins present in the culture supernatant were precipitated by the addition of 1/10 (vol/vol) trichloracetic acid. Electrophoresis in 10% polyacrylamide gels in the presence of sodium dodecyl sulfate (SDS-PAGE) was performed as described (Laemmli, 1970). After electrophoresis, proteins were either stained with Coomassie brilliant blue or transferred to a nitrocellulose membrane.

Immunoblotting procedures were carried out with mouse polyclonal anti-filaments antibodies. Horseradish peroxidase-labelled goat anti-mouse antibodies were used as secondary antibodies and visualized by enhanced chemiluminescence. The N-terminal sequence of VirA and IpaH9.8 and that of internal peptides, which were obtained by endolysin digestion and purified by chromatography, were determined by the Edman degradation procedure.

The β-galactosidase activity present in bacteria growing in laboratory media was assayed by using the substrate o-nitro-phenyl-β-D-galactoside (ONPG) as described (Platt et al, 1972). The β-galactosidase activity present in intracellular bacteria was assayed by using the substrate 4-methyl-umbelliferyl-β-D-galactoside (MUG) as described (Klarsfeld et al., 1994). Fluorescence was measured by using a Dynatec apparatus, with 365 nm excitation and 450 nm emission wavelengths. Activities were computed as fluorescence units per hour per bacterium; four fluorescence units were equivalent to one Miller unit and all results are presented in Miller units.

Genes Under Transcriptional Control of Type III Secretion Machinery

Using lacZ transcriptional fusions, we have investigated transcription of virA, of four members of the ipaH family, and of the ipaBCDA and mxi operons. We present evidence that transcription of virA and of four ipaH genes, but not that of the ipaBCDA and mxi operons, is increased when secretion through the type III secretion machinery is enhanced in response to addition of Congo red to the growth medium and to inactivation of ipaD. In addition, transcription of virA- and ipaH-lacZ fusions was activated during entry of bacteria into epithelial cells.

We used lacZ fusions to investigate transcription of virA, ipaH9.8, ipaH7.8, ipaH4.5, and ipaH1.4, as well as that of operons located in the entry region. Transcription of genes of the entry region was high in derivatives of the wild-type strain and was not increased in derivatives of the ipaD mutant or after growth in the presence of Congo red. These results indicate that: (i) the increased secretion observed with the wild-type strain growing in the presence of Congo red and with the ipaD mutant is not due to an increased transcription of the mxi operon; and (ii) transcription of mxi and ipaBCDA operations is the same whether the secretion machinery is poorly active (in the wild-type strain), or deregulated (by addition of Congo red or inactivation of ipaD). This transcriptional analysis and previous Western blot analysis, which indicated that similar amounts of IpaB and IpaC were present in wild-type, ipaD, and mxiD strains (Allaoui et al., 1993b; Ménard et al., 1993), suggest that expression of genes of the entry region is not controlled by the secretion machinery. In contrast, transcription of the virA and ipaH genes was low in derivatives of the wild-type strain and was increased during growth in the presence of Congo red and in derivatives of the ipaD mutant. These results, together with the low production of VirA in the ipaD mxiD mutant and the low transcription of virA in the mxiD mutant growing in the presence of Congo red, indicate that the secretion machinery is involved in the control mechanism of the virA promoter and suggest that transcription of virA and of four copies of the ipaH family is enhanced in response to an active secretion through the type III apparatus.

Similar amounts of β-galactosidase were present in bacteria carrying the ipgD-lacZ fusion prior to and after 60 min of infection. In contrast, the amount of β-galactosidase present in bacteria carrying virA and ipaH-lacZ fusions was about 10 times higher after 60 min of infection than prior to infection. Due to the period of incubation in the presence of gentamicin which is required to eliminate extracellular bacteria, we could not investigate whether virA and ipaH transcription was activated upon contact with or shortly after entry into epithelial cells. Only low amounts of β-galactosidase were present in bacteria carrying virA- and ipaH-lacZ fusions after 150 min of infection, which suggests that the virA and the ipaH genes had not been transcribed between 60 and 150 min of infection. Since there is a correlation between virA and ipaH transcription and active secretion, these results suggest that secretion might not be active when bacteria are multiplying in the cytoplasm of HeLa cells. Alternatively, signals other than secretion might affect negatively transcription of the virA and ipaH genes in the intracellular compartment.

The mechanism involved in the transcriptional control of the virA and ipaH genes in response to active secretion is not known yet. The low transcription of virA by the virA mutant indicates that virA is not autoregulated and the low production of VirA by the ipaD mxiD mutant suggests that IpaD is not the effector of the regulation of the virA promoter. When the secretion apparatus is inactive, a negative regulator might accumulate in the cytoplasm and repress virA and ipaH transcription. Secretion of this regulator, due to the lack of IpaD or in response to external inducers, would decrease its cytoplasmic concentration, thereby leading to the transcriptional activation of its target promoters. Secretion of a negative regulator as a mechanism for the control of gene expression has been documented in Salmonella and Yersinia. In *S. typhimurium*, transcription of the flagellin gene by an RNA polymerase containing the alternate sigma factor $\delta^{28}$ requires the integrity of the basal-hook body complex which constitutes an export apparatus related to type III secretion machineries. Secretion of the anti-sigma factor FlgM allows transcription of the flagellin gene by a $\delta^{28}$-containing RNA polymerase, thus coupling flagellin expression to flagellar assembly (Hughes et al. 1993; Kutsukake et al., 1994). In Yersinia, expression of the yop genes is down regulated when Yop secretion is compromised (Cornelis et al., 1987) and secretion of LcrQ via the type III secretion apparatus has been proposed to lead to the transcriptional activation of yop promoters by a mechanism which has not been characterized yet (Pettersson et al., 1996). Differences in the transcriptional regulation of genes encoding proteins secreted by the type III secretion machinery of Shigella are likely to reflect differences in the functional role of these secreted proteins during infection.

TABLE I

Shigella strains

| Strain | Genotype | Reference |
|---|---|---|
| M90T | wild type | Sansonetti et al., 1985 |
| M90T-Sm | spontaneous Sm$^R$ derivative of the M90T | Allaoui et al., 1992 |
| BS176 | plasmidless derivative of M90T | Sansonetti et al., 1985 |
| SF132 | icsB-lacZ in M90T-Sm | Allaoui et al., 1992 |
| SF134 | ipgD-lacZ in M90T-Sm | Allaoui et al., 1993a (C.N.C.M. No. I-2016)* |
| SF401 | mxiD | Allaoui et al., 1993b |
| SF403 | mxiD-lacZ in M90T-Sm | Allaoui et al., 1993b |
| SF622 | ipaD | Ménard et al., 1993 |
| SF623 | ipaA-lacZ in M90T-Sm | Ménard et al., 1993 |
| SF624 | ipaA-lacZ in SF622 (ipaD) | Ménard et al., 1993 |
| SF634 | ipaD mxiD | Ménard et al., 1994 |
| SF635 | ΔipaBCDA | Parsot et al., 1995 |
| SF803 | icsB-lacZ in SF622 (ipaD) | |
| SF806 | ipgD-lacZ in SF622 (ipaD) | (C.N.C.M. No. I-2017)* |
| SF808 | mxiD-lacZ in SF622 (ipaD) | |
| SF1001 | virA-lacZ in M90T-Sm (virA$^+$) | (C.N.C.M. No. I-2018)* |
| SF1002 | virA-lacZ in SF622 (virA$^+$) | (C.N.C.M. No. I-2019)* |
| SF1003 | virA-lacZ in M90T-Sm (virA$^-$) | |
| SF1004 | virA-lacZ in SF622 (virA$^-$) | |
| SF1005 | ipaH9.8-lacZ in M90T-Sm | |
| SF1006 | ipaH9.8-lacZ in SF622 (ipaD) | |
| SF1007 | ipaH7.8-lacZ in M90T-Sm | |
| SF1008 | ipaH4.5-lacZ in M90T-Sm | |
| SF1009 | ipaH4.5-lacZ in SF622 (ipaD) | |
| SF1010 | ipaH1.4-lacZ in M90T-Sm | |
| SP1011 | ipaH1.4-lacZ in SF622 (ipaD) | |
| SF1012 | virA-lacZ in SF401 (mxiD) | |

*Deposited in the Collection Nationale de Cultures de Microorganismes in Paris, France on May 13,1998.

TABLE II

Expression of lacZ transcriptional fusions by bacteria growing in vitro β-galactosidase activity (Miller units)$^a$

| Fusion | ipaD$^+$ | ipaD$^-$ | Ratio I$^b$ | ipaD$^+$ + CR | Ratio Ii$^c$ |
|---|---|---|---|---|---|
| virA-lacZ | 16 | 280 | 17 | 280 | 17 |
| virA-lacZ mxiD | 17 | NA | NA | 18 | 1.1 |
| ipaH9.8-lacZ | 28 | 580 | 21 | 325 | 12 |
| ipaH7.8-lacZ | 20 | NA | NA | 235 | 12 |
| ipaH4.5-lacZ | 31 | 360 | 12 | 110 | 3.5 |
| ipaH1.4-lacZ | 53 | 280 | 5.3 | 270 | 5.1 |
| ipaA-lacZ | 485 | 510 | 1.1 | 390 | 0.8 |
| icsB-lacZ | 290 | 305 | 1.1 | 285 | 1.0 |
| mxiD-lacZ | 275 | 260 | 0.9 | 320 | 1.2 |
| ipgD-lacZ | 450 | 400 | 0.9 | 475 | 1.1 |

$^a$Activities are the means of at least three independent experiments. Standard deviations are within 25% of the reported values.
$^b$Activity present in ipaD$^-$ strains versus activity present in ipaD$^+$ strains.
$^c$Activity present in derivatives of the ipaD$^+$ strain grown in the presence of Congo red versus activity present in the same strains grown in the absence of Congo red.
NA not applicable.

TABLE III

Expression of lacZ transcriptional fusions by intracellular bacteria β-galactosidase activity (Miller units)$^a$

| Fusion | in vitro | 60 min of infection | Ratio I$^b$ | 150 min of infection | Ratio II$^c$ |
|---|---|---|---|---|---|
| ipgD-lacZ | 450 | 490 | 1.1 | 463 | 1.1 |
| virA-lacZ | 16 | 280 | 18 | 49 | 5.7 |
| ipaH9.8-lacZ | 28 | 350 | 13 | 49 | 7.1 |
| ipaH7.8-lacZ | 20 | 590 | 30 | 150 | 3.9 |
| ipaH4.5-lacZ | 31 | 280 | 9.0 | 21 | 13.3 |
| ipaH1.4-lacZ | 53 | 300 | 5.7 | 49 | 6.1 |

$^a$Activities are the means of at least three independent experiments. Standard deviations are within 25% of the reported values.
$^b$Activity present after 60 min of infection versus activity present in bacteria grown in vitro.
$^c$Activity present after 60 min of infection versus activity present after 150 min of infection References Alfano, J. R. and Collmer, A. (1997) The type III (Hrp) secretion pathway of plant pathogenic bacteria: trafficking harpins, Avr proteins, and death. *J. Bacteriol*, 179, 5655–5662.

Allaoui, A., Mounier, J., Prévost, M.-C., Sansonetti, P. J., and Parsot, C. (1992) icsB: a *Shigella flexneri* virulence gene necessary for the lysis of protrusions during intercellular spread. *Mol. Micribiol.*, 6, 1605–1616.

Allaoui, A., Ménard, R., Sansonetti, P. J., and Parsot, C. (1993a) Characterization of the *Shigella flexneri* ipgD and ipgF genes, which are located in the proximal part of the mxi locus. *Infect. Immun.*, 61, 1707–1714.

Allaoui, A., Sansonetti, P. J., and Parsot, C. (1993b) MxiD: an outer membrane protein necessary for the secretion of the *Shigella flexneri* Ipa invasins. *Mol. Microbiol.*, 7, 59–68.

Andrews, G. P., and Maurelli, A. T. (1992) mxiA of *Shigella flexneri* 2a, which facilitates export of invasion plasmid antigens, encodes a homologue of the low-calcium response protein, LcrD, of *Yersinia pestis. Infect. Immun.*, 60, 3287–3295.

Bahrani, F. K., Sansonetti, P. J., and Parsot, C. (1997) Secretion of Ipa proteins by *Shigella flexneri*: inducer molecules and kinetics of activation. *Infect. Immun.*, 65, 4005–4010.

Bernardini, M. L., Mounier, J., d'Hauteville, H., Coquis-Rodon, M., and Sansonetti, P. J. (1989) Identification of icsA, a plasmid locus of *Shigella flexneri* that governs bacterial intra and intercellular spread through interaction with F-actin. *Proc. Natl. Acad. Sci. USA*, 86, 3867–3871.

Bernardini, M. L., Fontaine, A., and Sansonetti, P. J. (1990) The two-component regulatory system OmpR-EnvZ controls the virulence of Shigella. *J. Bacteriol.*, 172, 6274–6281.

Collazo, C. M., and Galan, J. E. (1997) The invasion-associated type III system of *Salmonella typhimurium* directe the translocation of Sip proteins into the host cell. *Mol. Microbiol*, 24, 747–756.

Cornelis, G., Vanooteghem, J.-C., and Sluiters, C. (1987) Transcription of the yop regulon from *Y. enterocolitica* requires trans-acting pYV and chromosomal genes. *Microb. Pathogen.*, 2, 367–379.

Hale, T. L. (1991) Genetic basis of virulence in Shigella species. *Microbiol. Rev.*, 55, 206–224.

Hartman, A. B., Venkatesan, M. M., Oaks, E. V., and Buysse, J. M. (1990) Sequence and molecular characterization of a multicopy invasion plasmid antigen gene, ipaH, of *Shigella flexneri*. *J. Bacteriol*, 172, 1905–1915.

Hughes, K. T., Gillen, K. L., Semon, M. J., and Karlinsey, J. E. (1993) Sensing structural intermediates in bacterial flagellar assembly by export of a negative regulator. *Science*, 262, 1277–1280.

Klarsfeld, A. D., Goossens, P. L., and Cossart, P. (1994) Five *Listeria monocytogenese* genes preferentially expressed in infected mammalian cells; plcA, purH, parD, pyrE and an arginine ABC transporter gene, arpJ. *Mol. Microbiol.*, 13, 585–597.

Kutsukake, K., Iyoda, S., Ohnishi, K., and Iino, T. (1994) Genetic and molecular analysis of the interaction between the flagellum-specific sigma factors in *Salmonella typhimurium*. *EMBO J.*, 13, 4568–4576.

Labrec, E. H., Schneider, H., Magnani, T. J., and Formal, S. B. (1964) Epithelial cell penetration as an essential step in the pathogenesis of bacillary dysentery. *J. Bacteriol.*, 88, 1503–1518.

Laemmli, U. K. (1970) Cleavage of structural proteins during the assembly of the head of bacteriophage T4. *Nature* (London) 227, 680–685.

Lett, M.-C., Sasakawa, C., Okada, N., Sakai, T., Makino, S., Yamada, M., Komatsu, K., and Yoshikawa, M. (1989) virG, a plasmid-coded virulence gene of *Shigella flexneri*: identification of the VirG protein and determination of the complete coding sequence. *J. Bacteriol.*, 171, 353–359.

Makino, S., Sasakawa, C., Kamata, K., Kurata, T, and Yoshikawa, M. (1986) A virulence determinant required for continuous reinfection of adjacent cells on the large plasmid in *Shigella flexneri* 2a. *Cell*, 46, 551–555.

Maurelli, A. T., Blackmon, B., and Curtiss, R (1984) Temperature-dependent expression of virulence genes in Shigella species. *Infect. Immun.*, 43, 195–201.

Maurelli, A. T., Baudry, B., d'Hauteville, H., Hale, T. L., and Sansonetti, P. J. (1985) Cloning of plasmid DNA sequences involved in invasion of HeLa cells by *Shigella flexneri*. *Infect. Immun.*, 49, 164–171.

Mescas, J., and Strauss, E. J. (1996) Molecular mechanisms of bacterial virulence: type III secretion and pathogenicity islands. *Emerg. Infect. Dis.*, 2, 271–288.

Ménard, R., Sansonetti, P. J., and Parsot, C. (1993) Nonpolar mutagenesis of the ipa genes defines IpaB, IpaC, and IpaD as effectors of *Shigella flexneri* entry into epithelial cells. *J. Bacteriol.*, 175, 5899–5906.

Ménard, R., Sansonetti, P. J., and Parsot, C. (1994) The secretion of the *Shigella flexneri* Ipa invasins is activated by epithelial cells and controlled by IpaB and IpaD. *EMBO J.*, 13, 5293–5302.

Parsot, C. (1994) *Shigeila flexneri*: genetics of entry and intercellular dissemination in epithelial cells. *Curr. Topics. Microbiol. Immunol.*, 192, 217–241.

Parsot, C., Ménard, R., Gounon, P., and Sansonetti, P. J. (1995) Enhanced secretion through the *Shigella flexneri* Mxi-Spa translocon leads to assembly of extracellular proteins into macromolecular structures. *Mol. Microbiol*, 16, 291–300.

Pettersson, J., Nordfelth, R., Dubinina, F., Bergman, T., Gustafsson, M., Magnusson, K. E., Wolf-Watz, H. (1 996) Modulation of virulence factor expression by pathogen target cell contact. *Science*, 273, 1231–1233.

Platt, T., Müller-Hill, B., and Miller, J. H. (1972) Assay of β-galactosidase. In Miller, J. H. (ed.), *Experiments in molecular genetics*. Cold Spring Harbor Laboratory, Cold Spring Harbor, N.Y., pp. 352–355.

Pope, L. M., Reed, K. E., and Payne, S. M. (1995) Increased protein secretion and adherence to HeLa cells by Shigella spp. following growth in the presence of bile salts. *Infect. Immun.*, 63, 3642–3648.

Rosqvist, R., Magnusson, K.-E., and Wolf-Watz, H. (1994) Target cell contact triggers expression and polarized transfer of Yersinia YopE cytotoxin into mammalian cells. *EMBO J.*, 13, 964–972.

Sankaran, K., Ramachandran, V., Subrahmanyam, Y. V. B. K., Rajarathnam, S., Elango, S., and Roy, R. K. (1989) Congo-red mediated regulation of levels of *Shigella flexneri* 2a membrane proteins. *Infect. Immun.*, 57, 2364–2371.

Sansonetti, P. J., Kopecko, D. J., and Formal, S. B. (1982) Involvement of a plasmid in the invasive ability of *Shigella flexneri*. *Infect. Immun.*, 35, 852–860.

Sansonetti, P. J., Ryter, A., Clerc, P., Maurelli, A. T., and Mounier, J. (1986) Multiplication of *Shigella flexneri* within HeLa cells: lysis of the phagocytic vacuole and plasmid-mediated contact hemolysis. *Infect. Immun.*, 51, 461–469.

Sasakawa, C., Kamata, K., Sakai, T., Makino, S., Yamada, M., Okada, N. and Yoshikawa, M. (1988) Virulence associated genetic region comprising 31 kilobases of the 230-kilobase plasmid in *Shigella flexneri* 2a. *J. Bacteriol.*, 170, 2480–2484.

Sasakawa, C., Adler, B., Tobe, T., Okada, V., Nagai, S., Komatsu, K., and Yoshikawa, M. (1989) Functional organization and nucleotide sequence of virulence region 2 on the large virulence plasmid of *Shigella flexneri* 2a. *Mol. Microbiol.*, 3, 1191–1201.

Sasakawa, C., Komatsu, K., Tobe, T., Suzuki, T., and Yoshikawa, M. (1993) Eight genes in region 5 that form an operon are essential for invasion of epithelial cells by *Shigella flexneri* 2a. *J. Bacteriol.*, 175, 2334–2346.

Sory, M.-P., and Cornelis, G. R. (1994) Translocation of an hybrid YopE-adenylate-cyclase from *Yersinia enterocolitica* into HeLa cells. *Mol. Microbiol.*, 14, 583–594.

Uchiya, K., Tobe, T., Komatsu, K., Suzuki, T., Watarai, M., Fukuda, I., Yoshikama, M., and Sasakawa, C. (1995) Identification of a novel virulence gene, virA, on the large plasmid of Shigella, involved in invasion and intercellular spreading. *Mol. Microbiol.*, 17, 241–250.

Van Gijsegem, F., Génin, S., and Boucher, C. (1993) Evolutionary conservation of pathogenicity determinants among plant and animal pathogenic bacteria. *Trends Microbiol.*, 1, 175–180.

Venkatesan, M. M., Buysse, J. M., and Hartman, A. B. (1991) Sequence variation in two ipaH genes of *Shigella flexneri* 5 and homology to the LRG-like family of proteins. *Mol. Microbiol.*, 5, 2435–2445.

Venkatesan, M. M., Buysse, J. M., and Oaks, E. V. (1992) Surface presentation of *Shigella flexneri* invasion plasmid antigens requires the products of the spa locus. *J. Bacteriol.*, 174, 1990–2001.

Watarai, M., Tobe, T., Yoshikawa, M., and Sasakawa, C. (1995) Contact of Shigella with host ceils triggers release of Ipa invasins and is an essential function of invasiveness. *EMBO J.*, 14, 2461–2470.

Wood, M. W., Rosquvist, R., Mullan, P. B., Edwards, M. H., and Galyov, E. E. (1996) SopE, a secreted protein of *Salmonella dublin*, is translocated into the target eukaryotic cell via a sip-dependent mechanism and promotes bacterial entry. *Mol. Microbiol.*, 22: 327–338.

Zierler, M. K., and Galan, J. E. (1995) Contact with cultures epithelial cells stimulates secretion of *Salmonella typhimurium* invasion proteins InvJ. *Infect. Immun.*, 63, 4024–4028.

We claim:

1. A method of screening for a molecule that activates or inhibits type III secretion machinery in gram-negative bacteria, wherein the method comprises:

a) contacting a molecule to be tested with *Shigella flexneri* cells having a type III secretion system and containing a reporter gene transcriptionally fused to a promoter ofa gene activated or regulated by the type III secretion machinery under conditions for activation of the promoter; and b) detecting the presence or activity of the product of the reporter gene;

wherein the reporter gene is lacZ, phoA, gfp, or luxAB, wherein the promoter is from the virA, ipaH9.8, ipaH7.8, ipaH7.5, and ipaH1.4 genes, and wherein detecting the presence or activity of the Product of the reporter gene indicates whether the sample molecule activates or inhibits type III secretion machinery.

2. The method as claimed in claim 1, wherein transcription of the reporter gene is increased when secretion through the type III secretion machinery is enhanced.

3. The method as claimed in claim 2, wherein the cells contain an ipaD gene that is inactivated.

* * * * *

UNITED STATES PATENT AND TRADEMARK OFFICE
CERTIFICATE OF CORRECTION

PATENT NO. : 6,696,249 B1
DATED : February 24, 2004
INVENTOR(S) : Demers et al.

It is certified that error appears in the above-identified patent and that said Letters Patent is hereby corrected as shown below:

Title page,
Item [73], Assignees, "Santa" should read -- Sante --.

Column 15,
Line 60, should read -- of a -- instead of "ofa".

Column 16,
Line 57, should read -- product -- instead of "Product".

Signed and Sealed this

Fifteenth Day of June, 2004

JON W. DUDAS
*Acting Director of the United States Patent and Trademark Office*